United States Patent [19]

Eugster et al.

[11] Patent Number: 5,536,504
[45] Date of Patent: Jul. 16, 1996

[54] ULTRAMICROEMULSIONS FROM SPONTANEOUSLY DISPERSIBLE CONCENTRATES CONTAINING XANTHOPHYLL ESTERS AND HAVING ANTITUMOR ACTIVITY

[75] Inventors: Carl Eugster, Riehen; Conrad H. Eugster, Walisellen; Walter Haldemann, Binningen, all of Switzerland; Giorgio Rivara, San Francesco Al Campo, Italy

[73] Assignee: Marigen S.A., Riehen, Switzerland

[21] Appl. No.: 345,687

[22] Filed: Nov. 21, 1994

[30] Foreign Application Priority Data

Nov. 19, 1993 [CH] Switzerland ............................ 3458/93

[51] Int. Cl.$^6$ ............................ A61K 37/02; A61K 9/127
[52] U.S. Cl. ............................................................ 424/450
[58] Field of Search ............................................... 424/450

[56] References Cited

PUBLICATIONS

Khachik et al "Separation of Carotenol Fatty Acid Esters by High Performance Liquid Chromatography" J. Chromatog. 449(1988) 119– 133.

Khachik et al "Separation and Identification of Caratemoids and Their Oxidation Products in the Extracts of Human Plasma" Annal. Chem. 1992 64, 2111–2122.

Primary Examiner—Nathan M. Nutter
Attorney, Agent, or Firm—Foley & Lardner

[57] ABSTRACT

Methods for treatment of tumours with ultramicroemulsions from spontaneously dispersible concentrates containing xanthophyll esters, and new esters with xanthophyll compounds and processes for their production are provided.

5 Claims, No Drawings

ULTRAMICROEMULSIONS FROM SPONTANEOUSLY DISPERSIBLE CONCENTRATES CONTAINING XANTHOPHYLL ESTERS AND HAVING ANTITUMOR ACTIVITY

The present invention relates to ultramicroemulsions from spontaneously dispersible concentrates containing xanthophyll esters, new esters with xanthophyll compounds, processes for their production, as well as their use for the treatment of tumours.

Surprisingly It has been found that the selected esters with xanthophyll compounds possess outstanding antitumour properties, particularly when these compounds have been incorporated into spontaneously dispersible concentrates, which if diluted with water or 5%-glucose solution form thermodynamically stable ultramicroemulsions having a hydrodynamic radius of 1,5 to 3 nm.

DESCRIPTION OF THE INVENTION

The term xanthophyll esters, as used in this invention, comprises selected esters with mono- and dihydroxycarotenes. These esters correspond to the formulae (I) to (VI):

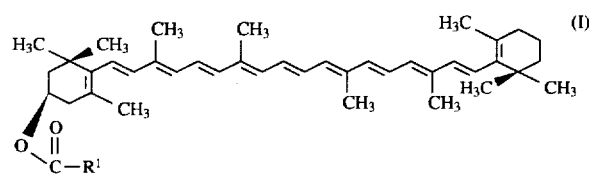

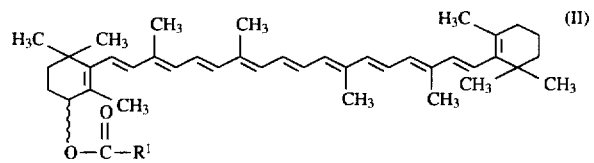

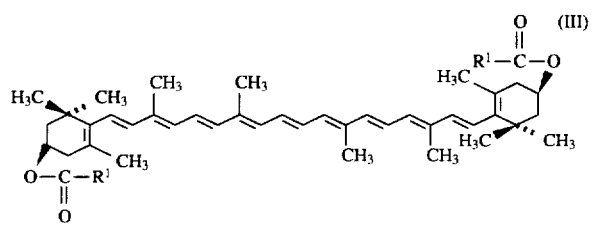

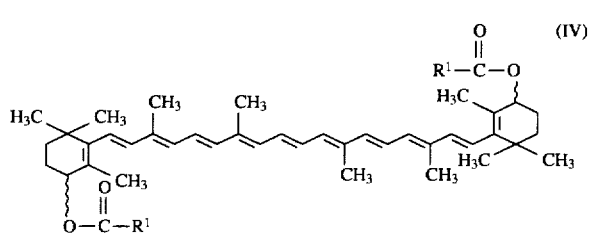

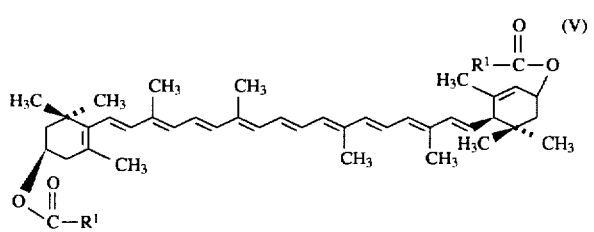

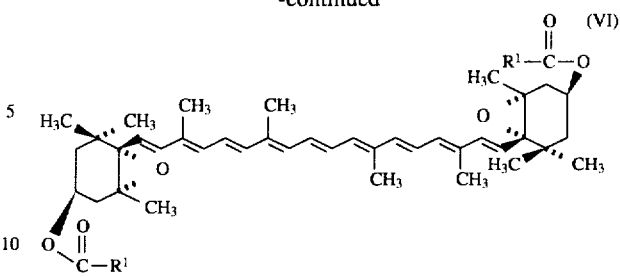

whereby in the formulae (I) to (VI) the radical $R^1$ represents a $C_1$ to $C_{32}$ alkyl or a $C_2$ to $C_{32}$ alkenyl and alkapolyene group or a $C_2$ to $C_{32}$ alkinyl group.

Compounds according to formulae (I) to (VI), in which the radical $R^1$ stands for a $C_2$ to $C_{32}$ alkenyl or alkapolyene group or a $C_2$ to $C_{32}$ alkinyl group, are new and form an integral part of the present invention.

The alkyl, alkenyl, alkapolyene or alkinyl groups at $R^1$ can be straight-chained or branched.

Preferred are those compounds according to formulae (I) to (VI), in which the radical $R^1$ stands for a $C_1$ to $C_{18}$ alkyl, a $C_2$ to $C_{18}$ alkenyl or alkapolyene or for a $C_2$ to $C_{18}$ alkinyl group. Most important are compounds according to the formulae (I) to (VI), in which the radical $R^1$ designates a $C_2$ to $C_{18}$ alkenyl and alkapolyene group respectively or a $C_2$ to $C_{18}$ alkinyl group.

The compounds according to formulae (I) to (VI) can be present in diverse stereoisomeric or rotational forms. Examples of compounds according to formulae (I) to (VI) are, inter alia:

(3R)-β,β-Carotene-3-ol-10-undecenoate
[β-Cryptoxanthin-10-undecenoate)]
β,β-Carotene-4-ol-10-undecenoate
[β-Isocryptoxanthin-10-undecenoate]
(3R)-β,β-Carotene-3-ol-palmitate
[β-Cryptoxanthin-palmitate]
(3R,3'R)-β,β-Carotene-3,3'-diol-di-n-valerate
[Zeaxanthin-di-n-valerate]
(3R,3'R)-β,β-Carotene-3,3'-diol-di-10-undecenoate
[Zeaxanthin-di-10-undecenoate]
(3R,3'R)-β,β-Carotene-3,3'-diol-di-palmitate
[Zeaxanthin-di-palmitate; Physalien]
β,β-Carotene-4,4'diol-di-10-undecenoate
[Isozeaxanthin-di-10-undecenoate]
(3R,3'R,6'R)-β,ε-Carotene-3,3'-diol-di-10-undecenoate
[Lutein-di-10-undecenoate; Xanthophyll-di-undecenoate]
(3R,3'R,6'R)-β,ε-Carotene-3,3'-diol-di-palmitate
[Lutein-di-10-palmitate; Xanthophyll-di-palmitate; Helenien](3S,5R,6S,3'S,5'R,6'S)-5,6,5',6'-Diepoxy-5,6,5',6'-tetrahydro-β,β-carotene-3,3'-diol-di-10-undecenoate
[Violaxanthin-di-10-undecenoate]

The newly synthetized compounds according to formulae (I) to (VI) can be manufactured according to the following procedures, which are known per se:

a) Reaction of a compound according to formula (VII):

$$R^4\text{---COOH} \qquad (VII)$$

in which $R^4$ stands for a $C_1$ to $C_{32}$ alkyl, a $C_2$ to $C_{32}$ alkenyl or alkapolyene group or a $C_2$ to $C_{32}$ alkinyl group, with N,N'-carbonyl-diimidazole at 0° to 50° C. under cover of protective gas and with the addition of a catalytic amount of an alcoholate, in an indifferent solvent or solvent mixture, and subsequent reaction of the imidazolides formed with one of the xanthophyll compounds according to the formulae (VIII) to (XIII):

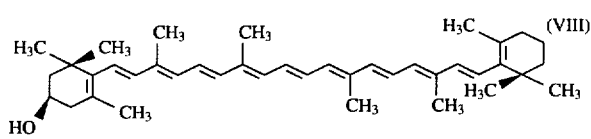

(3R)-β,β-CAROTENE-3-ol; CRYPTOXANTHIN, Cryptoxanthol, Caricaxanthin, Hydroxy-β-carotene, β-Carotene-3-ol, Physoxanthinneo-β-cryptoxanthin; Merck-Index 11.2612

Total synthesis: Islet et al., Helv. Chim.Acta 40, 456–467 (1957), All-trans-Cryptoxanthin, top. 158°–159° C.

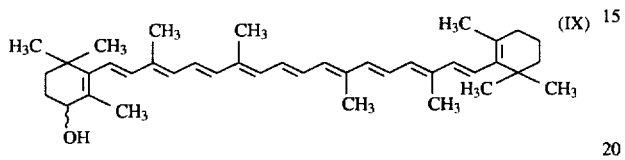

β,β-Carotene-4-ol; ISOZEAXANTHIN; 4-Hydroxy-β-carotene; Myxoxanthol; Aphanol.

Syntheses: J. D. Surmatis et al., Helv.Chim.Acta 53, 974–990 (1970). F. J. Petracek and L. Zechmeister, J.Am.Chem.Soc. 78, 3188 (1956). R. Entschel and P. Karrer, Helv.Chim.Acta 41, 983 (1958).

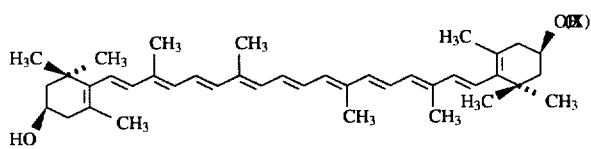

(3R,3R')-β,β-CAROTENE-3,3'-diol; ZEAXANTHIN, ZEAXANTHOL, Anchovyxanthin. mp. 207° C. (Zechmeister, Kuhn). Merck-Index 11.10019

Syntheses: R. Buchecker and C. H. Eugster, Helv.Chim.Acta 63, 2531 (1980). O. Isler et al., Helv.Chim.Acta 40, 456 (1957). O. Isler et al., Helv.Chim.Acta 39, 2041 (1956). E. Widmer et al., Helv.Chim.Acta 65, 958 (1982)

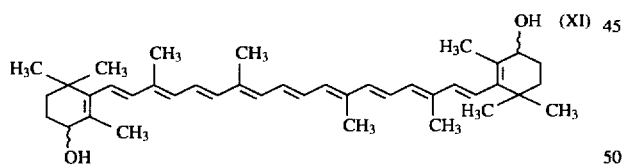

β,β-CAROTENE-4,4'-diol; ISOZEAXANTHIN, Aphanicol.

Syntheses: O. Isler et al., Helv.Chim.Acta 39, 449–445 (1956) A. Haag and C. H. Eugster, Helv.Chim.Acta 65, 1795–1803 (1982)

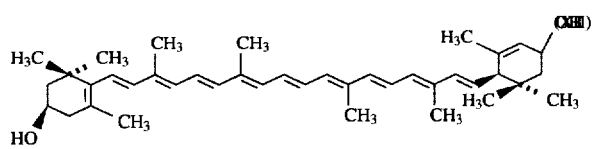

(3R,3'R,6'R)-β,ε-CAROTENE-3,3'-diol; LUTEIN, XANTHOPHYLL, LUTEOL, CUCURBITAXANTHIN, 3,3'-Dihydroxy-α-carotene. Merck-Index 11.9972

Synthesis: H. Mayer and A. Rüttimann, Helv.Chim.Acta 63, 1451–1455 (1980)

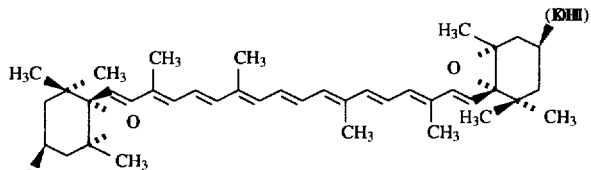

(3S,5R,6S,3'S,5'R,6'S)-5,6,5',6'-Diepoxy-5,6,5',6'-tetrahydro-β,β-CAROTENE-3,3'-diol; VIOLAXANTHIN, Diepoxy-ZEAXANTHIN, 9-cis-Violaxanthin. Merck-Index 11.9902

Partial synthesis: P. Karrer et al., Helv.Chim.Acta 28, 300 (1945)

b) Formation of the chloride and bromide respectively of a compound according to formula (VII)

in which $R^4$ represents a $C_1$ to $C_{32}$ alkyl, a $C_2$ to $C_{32}$ alkenyl or alkapolyene group or a $C_2$ to $C_{32}$ alkinyl group, with a chlorination and a bromination agent, respectively, such as, e.g., thionylchloride, oxalylchloride or oxalylbromide, and subsequent reaction with one of the compounds according to the formulae (VIII) to (XIII), at a temperature of 0° to 60° C. under cover of protective gas, in an indifferent solvent, such as toluene or tetrahydrofuran, and in the presence of a catalyst, such as, e.g., dimethylformamide or p-dimethylaminopyridine.

Surprisingly, the xanthophyll esters according to the formulae (I) to (VI) possess a remarkable antitumour activity, particularly so if they have been incorporated into spontaneously dispersible concentrates, which if diluted with water or 5%-glucose solution generate thermodynamically stable ultramicroemulsions, having a hydrodynamic radius of 1,5 to 3 nm. Therefore, spontaneously dispersible concentrates containing the xanthophyll esters according to formulae (I) to (VI) form an integral part of this invention.

The xanthophyll esters according to the formulae (I) to (VI) are compounds which are practically insoluble in water and form polymeric agglomerates. In order to enable the molecules of these compounds to penetrate through the membranes of tumour cells, to spread in the cell plasma and to become active, these compounds must first be properly solubilized in an aqueous medium. By preparing thermodynamically stable oil-in-water ultramicroemulsions, employing selected cotensides or hydrotropic agents on the one hand, and appropriate tensides on the other hand, it becomes possible to achieve an optimal degree of solubilization of these xanthophyll esters.

All experimental observations gained with stable microemulsions of this kind can be uniformly interpreted by means of the assumption that the system produces in the aqueous phase organized aggregates, which are called MICELLES. These micelies possess a more or less globular shape, having a hydrodynamic radius of less than 10 nm. They are thermodynamically stable. The tensides and cotensides are capable at the phase-boundary of the microemulsion of hindering SELF-DIFFUSION. This means that no mixing takes place between the outer aqueous phase of the microemulsion and the inner oily phase, which contains the dicarbonic acid ester compounds solubilized in the coemulgator and/or biotenside solvent.

The micelles, which contain in their inner phase the solubilized antitumor substances, are coated by a tenside layer or bilayer and are thus enabled first to penetrate the human skin and then to penetrate through the plasma membrane of the tumour cell. This diffusion process takes place on account of thermal molecular movements exclusively.

The volume and the speed of substance transport across the cell membranes are dependent upon the differential in concentration existing between the extracellular outside and the inside of the individual tumour cell. The diffusion flow continues along the concentration gradient until it is consumed and an equal concentration of active substance [or of a therapeutic system] is reached in both compartments, the extracellular zone and the internal zone. Such diffusion processes occur independently of any energy input from outside into the interacting compartments. They can show slow-release-effects. In biological systems they are not related to metabolic energy.

The speed of diffusion is governed by Fick's law of diffusion $$\frac{dm}{dt} \cdot \frac{1}{q} = -D \frac{dc}{dx} \quad \text{EQUATION (A)}$$

where dm signifies the amount in Mol of active substance molecules which penetrate a cell surface q (in cm$^2$) per time-unit dt (in seconds). D is the coefficient of diffusion and dc the concentration differential over the distance dx.

According to NERNST the diffusion coefficient is dependent on the absolute temperature and friction resistance $$D = \frac{R}{N} \cdot \frac{T}{f} = \frac{kT}{f} \quad \text{EQUATION (B)}$$

Friction resistance is, according to STOKE's law, $$f = 6\pi\eta r \quad \text{Equation (C)}$$

a function of the viscosity of the diffusing solution and of the radius of the diffusing particles. By substituting f with $f=6\pi\eta r$ in the Nernst equation, one obtains the SUTHERLAND-EINSTEIN equation for the DIFFUSION COEFFICIENT $$D = \frac{RT}{N} \cdot \frac{1}{6\pi\eta r} = \frac{kT}{6\pi\eta r} \quad \text{EQUATION (D)}$$

where k stands for the Boltzmann constant.

If for a particular diffusion process one assumes a regular reduction of concentration in the membrane of the tumor cell, then the expression $$\frac{dc}{dx}$$

in the diffusion law can be restated as $$\frac{\Delta c}{x} \quad \text{(= concentration difference } \Delta c \text{ over a membrane of thickness } x\text{)}.$$

x is a constant value for a specific membrane. For this reason, it can be combined with the diffusion coefficient to express a new constant, the permeability coefficient P:

$$P = \frac{D}{x} \quad \text{EQUATION (E)}$$

The expression $$\frac{dm}{dt} \cdot \frac{1}{q}$$

in the diffusion equation is called FLUX J. It has the dimension Mol per second per cm$^2$. The negative sign on the right side of the equation indicates that the transport of the molecules of the active substance or the systems preparation containing active substances flows in the direction of the decreasing concentration.

Therefore, we have $$J = -P\Delta c = -\frac{RT}{Nx} \cdot \frac{1}{6\pi\eta r} \cdot \Delta c = \frac{kT}{x} \cdot \frac{1}{6\pi\eta r} \cdot -\Delta c \quad \text{EQUATION (F)}$$

It can be deduced from this equation that the velocity of the diffusion process across the cell membrane is governed by:

1) the concentration difference $\Delta c$ in the two compartments
2) the radius of the particles of the diffusing active substance or system's preparation
3) the viscosity of the diffusing aqueous solution (emulsion)
4) the temperature.

The spontaneously dispersible concentrates prepared in accordance with the invention contain 0.001 to 30% by weight of individual xanthophyll esters according to the formulae (I) to (VI), and combinations of such compounds respectively 0 to 40% by weight of a solvent or solvent mixture which is pharmaceutically acceptable and acts as a hydrotropic agent or coemulsifier 0.001 to 90% by weight of a pharmaceutically acceptable surfactant or surfactant mixture, and optionally up to 10% by weight of a vitamin or provitamin up to 10% by weight of a penetration enhancer and/or stabilizer, and, if appropriate, customary excipients and/or diluents.

The surfactants or surfactant mixtures to be employed according to the invention can be anionic, cationic, amphoteric or non-ionic. Ideally, they are non-ionic and have an HLB-value (i.e. a hydrophilic-lipophilic balance) of between 2 and 18; preferably, it is between 2 and 6 on the one hand and 10 and 15 on the other hand. HLB values describe the hydrophilic and lipophilic properties of an emulsifier. In this context see "Hydrophile-Lipophile Balance: History and recent Developments" by Paul Becher in Journal of Dispersion Science and Technology, 5 (1), 81–96 (1984).

Suitable anionic surfactants can be both socalled water-soluble soaps and water-soluble synthetic compounds.

Suitable soaps are the alkali metal salts, alkaline earth metal salts or optionally substituted ammonium salts of higher fatty acids ($C_{12}$ to $C_{22}$), for example the natural Na or K salts of oleic or stearic acids, or of natural mixtures of fatty acids which can be obtained, inter alia, from coconut oil or tallow oil. Other surfactants which may be mentioned are fatty acid methyltaurine salts, and modified and non-modified phospholipids.

However, more frequently used surfactants are so-called synthetic surfactants, in particular fatty sulfonates, fatty sulfates, sulfonated benzimidazole derivatives or alkylarylsulfonates.

The fatty sulfonates and fatty sulfates are usually present in the form of alkali metal salts, alkaline earth metal salts or optionally substituted ammonium salts and generally have an alkyl radical containing 8 to 22 C atoms, alkyl also encompassing the alkyl moiety of acyl radicals. Examples are the Na or Ca salt of ligninsulfonic acid, of dodecylsulfuric ester and sulfonic acids of fatty alcohol/ethylene oxide adducts. The sulfonated benzimidazole derivatives preferably contain two sulfonyl groups and one fatty acid radical containing about 8 to 22 C atoms. Alkylarylsulfonates are, for example, the Na, Ca or triethanolamine salts of dodecylbenzenesulfonic acid, of dibutylnaphthalenesulfonic acid or of a naphthalenesulfonic acid/formaldehyde condensation product.

The non-ionic surfactants are mainly chosen from amongst the polyglycol ether derivatives of aliphatic or cycloaliphatic alcohols, saturated or unsaturated fatty acids and alkylphenols which can contain 3 to 30 glycol ether groups and 8 to 20 C atoms in the (aliphatic) hydrocarbon radical and 6 to 18 C atoms in the alkyl radical. Other suitable non-ionic surfactants are the water-soluble polyethyleneoxy-adducts onto polypropylene glycol and alkyl polypropylene glycol with 1 to 10 C atoms in the alkyl chain, which adducts contain 20 to 250 ethylene glycol ether groups and 10 to 100 propylene ether groups. The compounds which have been mentioned customarily contain 1 to 5 ethylene units per propylene glycol unit.

The following may be mentioned as examples of non-ionic surfactants: nonylphenol polyethoxyethanols, castor oil polyglycol ethers, polypropylene/polyethylene oxide adducts, tributylphenoxy-polyethoxy-ethanol, polyethyleneglycol and octylphenoxy-polyethoxyethanol. Moreover, fatty acid esters of polyoxyethylene-sorbitan, such as polyoxyethylene sorbitan trioleate, are also suitable.

The cationic surfactants are mainly quaternary ammonium salts which contain at least one alkyl radical having 8 to 22 C atoms as the N-substituent and which have lower, optionally halogenated alkyl radicals, benzyl radicals or lower hydroxyalkyl radicals as further substituents. The salts are mainly present in the form of halides, methylsulfates or ethylsulfates, for example stearyltrimethylammonium chloride or benzyldi-(2-chloroethyl)-ethyl-ammonium bromide.

When preparing the inventive spontaneously dispersible concentrates, special preference is given on the one hand to phosphoric acid ester tensides, such as:

Tristyrylphenolpolyoxyethylene-18-mono/dimethyl-phosphoric-acid-ester (Soprophor® FL, Rhône-Poulenc);

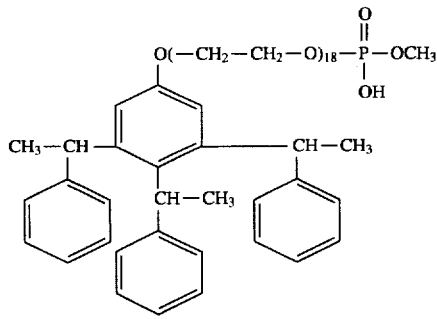

Soprophor FL (Rhône-Poulenc)

Nonylphenol-10-polyoxyethylene-mono/dimethylphosphoric-acid-ester (Diphasol® 3873, CIBA-GEIGY); or the identical Sermul® EA 188 (SERVO)

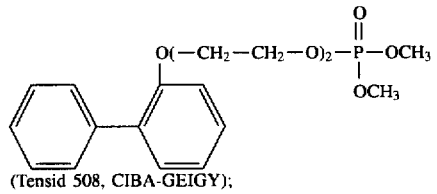

(Tensid 508, CIBA-GEIGY);

Tinovetin® JU (CIBA-GEIGY), a hydroxybiphenyll-10-ethoxy-phosphoric acid ester

Butyl-mono-4-ethoxy-phosphoric acid ester (Zerostat® AT, CIBA-GEIGY), and

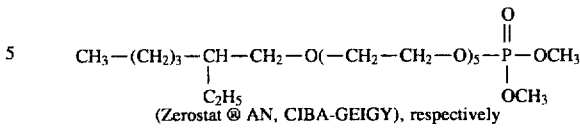

(Zerostat® AN, CIBA-GEIGY), respectively and on the other hand to betain compounds, i.e. amphoteric, salt- and waterfree imidazole derivatives, having an isoelectric/isoionic point near 7, such as e.g.

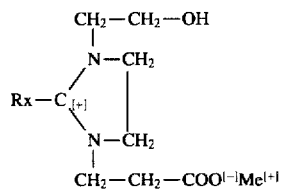

in which Me[+] stands for hydrogen, alkali and/or earth alkali atoms, and $R_x$ for $C_1$ to $C_{32}$ alkyl or $C_2$ to $C_{32}$ alkenyl group.

Furthermore, so-called "multi-functional glucose derivatives", such as, e.g., Glucate® SS (Methyl-glucose-sesquistearate) and Glucamate® SSE-20 (PEG-20-methyl-glucose-sesquistearate) of Amerchol, Edison, N. J., are also being used.

The following compounds may be employed as the pharmaceutically acceptable solvent which acts as the hydrotropic, or coemulsifier, for example: esters of an aliphatic alcohol ($C_3$ to $C_{18}$) with an aliphatic carboxylic acid ($C_{10}$ to $C_{22}$), such as isopropyl laurate, hexyl laurate, decyl laurate, isopropyl myristate and lauryl myristate; hydrocarbons having a straight carbon chain ($C_{12}$ to $C_{32}$) which is substituted by 6 to 16 methyl groups and which can have up to 6 double bonds, examples which may be mentioned being terpenes, such as polymethylbutanes and polymethyl-butenes.

Monoesters of ethylene glycol or propylene glycol with an aliphatic carboxylic acid ($C_6$ to $C_{22}$), such as propylene glycol monolaurate and propylene glycol monomyristate.

Esters of an aliphatic alcohol ($C_{12}$ to $C_{22}$) with lactic acid, such as, for example, myristyl lactate or, preferably, lauryl lactate. Monoesters or diesters of glycerol with an aliphatic carboxylic acid ($C_6$ to $C_{22}$), such as, for example, glyceryl caprylate or Miglyol® 812 neutral oil (Oleum neutrale).

Esters of a poly(2-7)ethylene glycol glycerolether having at least one free hydroxyl group with an aliphatic carboxylic acid ($C_6$ to $C_{22}$), such as, for example, aliphatic alcohols ($C_{12}$ to $C_{22}$), thus, inter alia, dodecanol, tetradodecanol, oleyl alcohol, 2-hexyldecanol and 2-octyl-decanol.

Esters containing at least one free hydroxyl group, of poly-(2-10)glycol with an aliphatic carboxylic acid ($C_6$ to $C_{22}$), monoethers of a polyethylene glycol with an aliphatic alcohol ($C_{12}$ to $C_{18}$), such as, for example, polyoxyethylene($C_{10}$)octylether.

Heterocyclic compounds such as 1-methyl-2-pyrrolidon. Biotenside esters according to the general formula:

$$R^2-COO-R^3$$

in which $R^2$ stands for citronellyl, geranyl, farnesyl, phytyl or isophytyl and $R^3$ means a $C_1$ to $C_{32}$ alkyl and a $C_{32}$ to $C_{32}$ alkenyl group respectively.

Before their application in the spontaneously dispersible concentrates all technical tensides have been cleaned by filtration or by chromatography over aluminum-oxide with an inert solvent as eluent, such as tetra-hydrofurane, ethyl alcohol or dichloromethane.

Suitable additives for the spontaneously dispersible concentrates according to the invention are vitamins and provitamins [such as, for example, vitamin A (retinoic acids), retinol, carotenes, tocopherols], as well as selected penetration enhancers ("Flux enhancers") and radical scavengers.

The daily dose required for pharmaceutical administration is 0.001 to 25 mg/kg of body weight, if possible split into 2–3 individual doses. For this purpose, the new xanthophyll esters, or the spontaneously dispersible concentrates with these compounds, can be incorporated into the conventional pharmaceutical preparations and dosage forms, such as coated tablets, tablets, capsules, powders, granules, pellets, solutions, ampuls, emulsions, creams or suppositories together with the customary excipients and/or diluents and stabilizers.

The active substances or mixtures of active substances which form the subject-matter of the invention, and the spontaneously dispersible concentrates which contain these active substances or mixtures of active substances, can be administered to humans orally, by injection (intravenously, subcutaneously or intramuscularly) or in other ways. If they are presented as solid dosage forms for oral administration, this can be in the form of tablets, granules, pellets, powders or capsules, etc. The preparations can contain additives, for example a pharmaceutical excipient, such as a saccharide or cellulose base, a binder, such as starch paste or methylcellulose, a filler, or a disintegrant, etc., with additives being employed which are customarily used in the preparation of medicinal or pharmaceutical formulations. When the active substances or mixtures of active substances according to the invention are administered orally in the form of liquid dosage forms, they can be present in any form selected from amongst aqueous preparations for internal use, from suspensions, emulsions and syrups, etc., and they can also be present in the form of dried preparations which are dissolved or emulsified prior to use.

When the active substances or mixtures of active substances according to the invention are processed in the form of aqueous solutions, suspensions or oily or aqueous emulsions, preferably microemulsions, from the spontaneously dispersible concentrates according to the invention, they can also be injected. However, it is customary to prepare the injection solutions shortly before administration, by dissolving or suspending the extracts or concentrates in aqueous, liquid media, such as sterile water or physiological sodium chloride solution or glucose solution.

If required, conventionally used solvents, stabilizers, preservatives and additives for the preparation of isotonic solutions can be added to a preparation for injection. The preparations for injection obtained in this manner are administered intravenously, intramuscularly, subcutaneously or in any other suitable way.

The present invention also relates to pharmaceutical preparations which contain the active substances, or mixtures of active substances, or the spontaneously dispersible concentrates, which have been above described, for controlling the growth of tumour cells. The pharmaceutical preparations according to the invention are those which can be used for enteral (such as oral or rectal) or for parenteral or topical administration to warm-blooded animals, which preparations contain the spontaneously dispersible concentrate on its own or together with a pharmaceutically acceptable excipient.

The dosage of the concentrates according to the invention depends on the warm-blooded species, on the age and on the individual condition, and on the mode of administration. For example, doses in the range of about 0.1–50 mg/kg of body weight are administered subcutaneously, and doses in the range of 0.05–5 mg/kg of body weight are administered intraperitoneally to warm-blooded animals having a low body weight, such as, for example, mice, rats and hamsters, to achieve an effect of tumour cell destruction.

The oral and rectal forms of the novel pharmaceutical preparations contain between 1 and 95%, preferably between 10 and 95%, and in particular between 20 and 95%, of the spontaneously dispersible concentrate according to the invention. For example, they can be present in unit-type dosage forms, i.e., as coated tablets, micropellets, tablets, suppositories or ampuls and, in particular, as capsules.

Suitable pharmaceutically acceptable excipients for the oral forms are mainly fillers, such as sugars (for example lactose, sucrose, mannitol or sorbitol), cellulose preparations and/or calcium phosphates (for example tricalcium phosphate or calcium hydrogen phosphate), furthermore binders, such as starch paste, with the use of, inter alia, corn starch, wheat starch, rice starch or potato starch, gelatin, tragacanth, methylcellulose, hydroxymethylcellulose, sodium carboxymethylcellulose and/or polyvinyl-pyrrolidone and/or disintegrants (if desired), such as the above mentioned starches, furthermore carboxy-methyl starch, crosslinked polyvinylpyrrolidone, agar, alginic acid or a salt thereof, for example sodium alginate.

Examples of suitable flow-control agents are the polyethylene glycols Nos. 200–600 and above.

The gelatin capsules, which are still the preferred dosage form for humans, are provided with suitable coatings, concentrated sugar solutions [which can optionally contain gum arabic, talc, polyvinylpyrrolidone, polyethylene glycol and/ or titanium dioxide], lacquer solutions (aqueous or those which have been prepared using organic solvents), or enteric coatings of solutions of suitable cellulose preparations, such as microcrystalline cellulose (Avicel®), acetylcellulose phthalate, hydroxymethylcellulose-phthalate, Metolose®, AQOAT® or a copolymer, such as Eudragit® L 30 D, being used, inter alia.

Pharmaceutical dosage forms for oral use which are particularly suitable according to the invention are two-piece gelatine capsules with a plasticizer, such as glycerol or sorbitol. The soft-gelatine or hard-gelatine capsules and the capsules made of AQOAT® (hydroxypropyl methylcellulose) respectively can contain the spontaneously dispersible concentrate according to the invention as a mixture with fillers, such as lactose, binders, such as starch, and/or glidants, such as talc or magnesium stearate, and, if appropriate, together with stabilizers and antioxidants, such as, for example, $\alpha,\beta$- or $\gamma$-tocopherol. It may be expedient to employ suitable liquids, such as liquid polyethylene glycols Nos. 200 to 600 as diluents, to which stabilizers and antioxidants can also be added.

For parenteral administration, distilled water is added to the concentrates according to the invention. To the aqueous microemulsion for injection which then forms, there can be added viscosity-increasing substances, for example Na-carboxymethyl-cellulose, sorbitol, mannitol and/or dextran, and if appropriate also stabilizers and antioxidants.

The pharmaceutical preparations for parenteral administration preferably contain between 0.1 and 60%, especially between 1 and 40%, of the spontaneously dispersible concentrate according to the invention.

Suitable preparations for topical use, which are particularly suitable for the prophylaxis and the treatment of cancers of the skin, are, for example, creams, ointments, pastes, foams, tinctures and solutions, which contain between 0.001 and 70% of the concentrate according to the invention.

Oily bases which are used for creams and oil-in-water emulsions which contain more than 50% water, are mainly fatty alcohols, for example lauryl alcohol, cetyl alcohol or stearyl alcohol, waxes of liquid to solid consistency, for example isopropyl myristate, wool wax or beeswax and/or hydrocarbons, such as, for example, petroleum jelly (petrolatum) or paraffin oil. Substances which are mainly suitable for emulsifying these oily bases are surface-active, pharmaceutically acceptable substances having predominantly hydrophilic properties, such as, for example, non-ionic emulsifiers, in particular fatty acid esters of polyalcohols or ethylene oxide adducts (such as polyglycerol fatty acid esters or polyethylene sorbitan fatty acid esters) having an HLB value of less than 8. Additives which are added to the water phase are, inter alia, agents which prevent desiccation of the creams, for example polyalcohols, such as glycerol, sorbitol, propylene glycol and/or polyethylene glycols Nos. 200 to 600, and furthermore preservatives, odor-imparting substances, etc. Ointments are water-in-oil emulsions which contain up to 70%, but preferably between 20 and 50%, water or aqueous phases.

Substances which are suitable as the lipid phase are mainly hydrocarbons, for example petroleum jelly, paraffin oil and/or solid paraffins, which contain hydroxy compounds suitable for improving the water-binding capacity, for example fatty alcohols or esters, such as cetyl alcohol or wool wax alcohols. In some cases, emulsifiers having an HLB-value of 8 to 16, such as, for example, sorbitan fatty acid esters (such as sorbitan isostearol) are also added. Additives which are added to the water phase are, inter alia, humectants, such as polyalcohols (glycerol, propylene glycol, sorbitol and/or polyethylene glycols No. 200, 400, 600); and furthermore preservatives, odor-imparting substances, etc.

Fatty ointments are anhydrous and chiefly contain hydrocarbons as the base, for example paraffin, petroleum jelly and/or liquid paraffins; moreover natural or partially-synthetic fats, such as, for example, coconut fatty acid triglyceride, furthermore: fatty acid partial esters of glycerol, such as, for example, the fatty alcohols, emulsifiers and/or additives which increase the water-absorption capacity, all of which have been mentioned in connection with the ointments.

Pastes are creams and ointments containing powder constituents which absorb secretions, such as, for example, metal oxides (such as titanium oxide or zinc oxide), and furthermore talc and/or aluminum silicates whose task it is to bind any moisture or discharge which may be present.

Foams are administered from pressurized containers and are oil-in-water emulsions of the spontaneously dispersible concentrates according to the invention which are present in aerosol form, with halogenated hydrocarbons (such as, for example, lower chloro-fluoroalkanes; such as dichloro-difluoromethane and dichlorotetra-fluorethane) being added as propellants. Other substances which may be added are the customary additives, such as preservatives, etc.

The present invention also relates to the use of the active substances, mixtures of active substances and spontaneuosly emulsifiable concentrates according to the invention for inhibiting the growth of tumour cells or as prophylactic agents against oncoses in humans and animals, administration preferably being carried out in the dosage forms which correspond to the pharmaceutical preparations described above.

PROCESSING EXAMPLES for the preparation of XANTHOPHYLL ESTERS according to the formulae (I) to (VI):

a) Preparation of β,β-Carotene-4,4'-diol-di-10-undecenoate (Isozeaxanthin-di-10-undecenoate)

1.0 Preparation of Isozeaxanthin

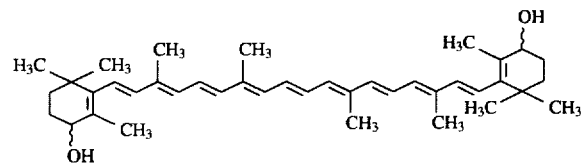

1.1 By reduction of CANTHAXANTHIN

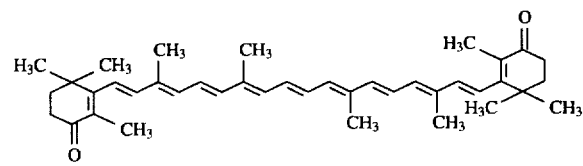

[Synthesis: P. Zeller et al., Helv.Chim.Acta 42, 841–842 (1959)] with DIBAH (Diisobutyl aluminumhydride pract.); Procedure following indications made by Prof. Dr. C. H. EUGSTER, University of Zurich.

In a 1 liter 4-neck round-bottom flask with $N_2$-inlet, magnetic stirrer, refluxing cooler and septum one dissolves 3,8 g Canthaxanthin trans. (FLUKA 21'385; Beil. 7, IV, 2680; Merck-Index 11.1756) with 120 ml tetrahydrofuran abs. and 380 ml ether abs. The solution is cooled down to 0° C. If the Canthaxanthin is not fully dissolved, this does not matter for the ensuing reduction. With a syringe, one adds dropwise 7 ml DIBAH, under good stirring. The solution remains clear for some time, and there is no visible reaction. One stirrs for 1 h at 0° C., and then lets the temperature rise to room temperature and stands the mixture for another hour. Now, one carefully adds small pieces of ice for hydrolisation and stirs until all aluminum hydroxide has precipitated. Add celite and pass through the funnel, washing extensively with ether/methanol (4:1). The red filtrate is evaporated gently, the residue dissolved in a little ethyl acetate, filtered again if necessary, evacuated and then crystallized from ethyl acetate/hexane. One obtains red crystals; mp. 157°–160° C. Yield: 3.02 g=79%. UV λmax. (ethanol qualitatively): 451.5, 478 nm; (ether qualitatively): 449.5, 477.5 nm. IR (KBr): free of carbonyl bands.

The mixture contains the meso and racemic forms, the separation of which is difficult and was not described up to now. In a micropreparative way, it can be effected as follows: column Spherisorb-S5-CN 4.3×250 mm (R. Bischoff, Stuttgart); eluent 80–90% hexane with 0,1% Et(i-propyl)$_2$N, 10–20% $CH_2Cl_2$ (with 1% methanol), flow 1 ml/min. Two peaks showing almost equal amounts of the meso and racemic-forms appear, the retention time of the meso form being shorter. Mp. of the meso-form 145°–146° C. (ex $CH_2Cl_2$/hexane), UV λmax. (ether) sh. 425, 448 (140'000), 475 (124'000). Racemic form mp. 140°–141° C.; UV λmax. (ether) sh. 425, 448 (146'600), 475 (130'600). The $^1$H-NMR spectra of the two isomers are identical also at 400 Mhz. The meso form can be concentrated in the lead fraction by repeated recrystallisation.

The reduction of Canthaxanthin to Isozeaxanthin can also be achieved with different hydride donators, such as $LiAlH_4$ (F. J. Petracek, L. Zechmeister, J.Amer.Chem.Soc. 1956, 78, 1427, yield of crystalline Isozeaxanthin 60%, or with $NaBH_4$ (yield 60–70%, our assays). Reduction with DIBAH renders the best yields and is the simplest of these methods.

1.2 Production and characterization of Isozeaxanthin-bis-Esters

Remark

The esterification follows, in principle, the method of Entschel and Karrer for the diacetylisation of Isozeaxanthin (Helv.Chim.Acta 1958, 41, 402), with the following changes, which are important to obtain good yields:

1) Use of a solvent, which permits the separation by precipitation of crystalline pyridine hydrochloride during the reaction.
2) Avoidance of water during the preparation.
3) Chromatography with an absorbent which is less basic than $ZnCO_3$.

Isozeaxanthin esters, particularly the higher ones, are very sensitive towards nucleophile and basic solvents. The contact with methanol, e.g. causes the transformation into 4,4'-Dimethoxy-$\beta,\beta$-carotene (cf. Entschel and Karrer, l.c.). As compared to 4,4', Diacetoxy-$\beta,\beta$-carotene, the esters with fatty acids of middle and higher chain lengths react even more rapidly, a fact which points to a $S_N2$-reaction.

With unexpected rapidity, there occur also elimination reactions in contact with silica gels of diverse qualities/sources, on thin layer as well as column chromatography. These reactions produce hydrocarbons of the type of the 3,3',4,4'-tetradehydro-$\beta,\beta$-carotene, as well as of the retro-dehydro-$\beta,\beta$-carotene. These compounds have a high Rf-value and feign on the DC the presence of double esters. There appearance is due to $S_N1$-reactions. If the silica gel is buffered with a base such as ethyldiisopropylamine, the elimination is also furthered.

1.3 General procedure

Take a 4-neck round-bottom flask with $N_2$-inlet, magnetic stirrer, reflux cooler and septum and add under water exclusion 200 mg of pure Isozeaxanthin (dried in oil vacuum) to a mixture of 0.5 ml pyridine abs. and 2 ml dichloromethane abs., and give to this solution 3 ml methylcyclohexane. After cooling down to 0° C. under protection from light and under good stirring, add 2 equivalents of acid chloride through the septum, using an injection syringe. Then let the mixture rise to room temperature under continuous stirring. After about 20 h, the precipitated pyridine chloride is syphoned off, wash with benzene and concentrate under vacuum the deep red solution.

The residue is now digested with about 6 ml of a mixture of benzene/petrol ether 2:1, and the partition in solution is brought to a column, packed dry with $CaCO_3$ (Merck, article 2066), size of the column: 2.8×16 cm, prewashed with benzene/petrol ether (1:4) and developed with the same eluent. In front, there is a small clear yellow zone, which can be eliminated. Then comes the brownish-orange main zone with the ester in question. Above this, there is unreacted educt and its half-ester. At the start, we have red derivatives resulting from deterioration. After concentration of the main zone, one obtains the practically pure ester as a deep reddish oil, with varying propensity to crystallisation. After drying, ca. 95% yield. Recrystallisation is possible after dissolution in 1.6 ml hot benzene and mixing, with 2 ml acetonitrile abs. and storing at −20° C.

1.4 We prepared the following Isozeaxanthin double esters:
Isozeaxanthin-di-Capronate
Isozeaxanthin-di-10-Undecenoate
Isozeaxanthin-di-Laurate
Isozeaxanthin-di-Palmitate (Isophysalien)

The analytical data for these esters are given in the technical Annexure 1/1.

1.5 By direct production from $\beta,\beta$-carotene (Provitamin A) Making use of the Entschel-Karrer procedure, it is possible to produce esters of Isozeaxanthin starting directly from $\beta,\beta$-carotene as basis and avoiding the step with Canthaxanthin. The reaction with N-bromosuccinimide is effected in the presence of an excess of a higher carbonic acid. The yields are significantly lower, though, which can in part at least be attributed to the requirement of complicated purification procedures.

b) Preparation of (3R,3'R)-$\beta,\beta$-Carotene-3,3'-diol-di-10-undecenoate (Zeaxanthin-di-10-undecenoate)

To 57 mg of Zeaxanthin [$\beta,\beta$-CAROTENE-3,3'-diol, all trans-$\beta$-Carotene-3,3'-diol; (3R,3'R)-dihydroxy-$\beta$-Carotene, Mw. 568.85, $C_{40}H_{56}O_2$, Merck-Index 11.10019

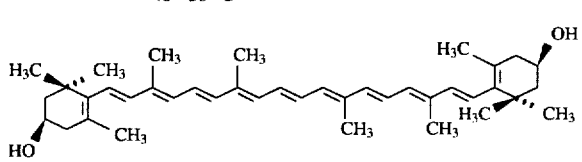

(Synthesis cf. R. Buchecker and C. H. Eugster, Helv.Chim.Acta 63 2531 (1980) and 50 mg dimethylformamide in 20 ml toluene, kept at 0° C. and under cover of protective gas, one adds dropwise 60 mg 10-undecenoyl chloride in 10 ml toluene. After stirring for 4 hours at 30° to 40° C., the toluene is being evacuated on a Rotavapor. The residue is chromatographed on a silicagel column with hexane/ethyl acetate as eluent (90:10).

After recrystallisation from acetonitrile one obtains the ZEAXANTHIN-di-10 -UNDECENOATE, having a melting point of 102° C., in the form of deeply red crystals; $R_f$-value in TLC plate hexane/ethyl acetate (80:20): 0,94. UV-absorption $\lambda$max. at 483,5 nm (in dichloromethane).

In analogous manner, the following compound is can also be obtained

| | | |
|---|---|---|
| ZEAXANTHIN-DI-n-VALERATE | UV $\lambda$max. 458,0 nm | |
| | mp. 79,3° C. | |
| ZEAXANTHIN-DI-LAURATE | | |
| ZEAXANTHIN-DI-PALMITATE (Physalien) | | |
| ZEAXANTHIN-DI-OLEATE | | |
| ZEAXANTHIN-DI-LINOLEATE | | |
| IR-Spectrum for Zeaxanthin-di-laurate | 2927 cm$^{-1}$ | $\nu$ (CH) |
| | 2855 " | $\nu$ (CH) |
| | 1725 " | $\nu$ (C=O) ester |
| | 1695 " | $\nu$ (C=C) |
| | 1465 " | $\delta$ (CH) |
| | 1377 " | $\delta$ (CH$_3$) |
| | 1174 " | $\nu$ (C—O) |
| | 975 " | $\delta$ (CH) trans disubst. C=C [olef. (CH)] | c) Preparation of Cryptoxanthin-di-10-undecenoate

To 55 mg of All-trans Cryptoxanthin (Synthesis: Isler et al., Helv.Chim.Acta 40, 456–467 (1957) and 50 mg dimethylformamide in 15 ml toluene, one adds dropwise at 0° C. and under cover of protective gas, 40 mg (excess) of 10-undecenoyl chloride in 10 ml toluene. After stirring for 4 hours at 30° C. the solvent toluene is evacuated on a Rotavapor and the residue is taken up on a silicagel column and chromatographed with hexane/ethyl acetate as eluent (90:10).

After recrystallisation from acetonitrile, one obtains the all-trans Cryptoxanthin-di-undecenoate in the form of yellow-orange, fluffy crystals, having a melting range from 56,3 to 62° C. Melting point 59,8° C. U.V.absorption at λmax. 460,2 nm (Dichloromethane).

d) Preparation of (3S,5R,6S,3′S,5′R,6′S)-5,6,5′,6′-Diepoxy- 5,6,5′,6′-tetra-hydro-β,β-carotene-3,3′-diol-di-10-undecenoate [Violaxanthin-di-10-undecenoate]

To 60 mg of Violaxanthin

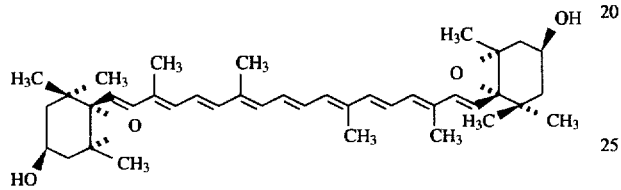

[Partial synthesis P. Karrer et al., Helv.Chim.Acta 28, 300 (1945)], (Merck-Index 11.9902) and 50 mg dimethylformamide in 20 ml of toluene one adds dropwise at 0° C. and under cover of protective gas, 60 mg (excess) of 10-undecenoyl chloride in 15 ml of toluene. After stirring for 4 hours at 30° to 40° C. the toluene is being evacuated. The residue is taken up on a silicagel column and chromatographed with hexane/ethyl acetate (90:10) as eleuent. One obtains the compound:

Violaxanthin-di-undecenoate.

Refractive index (RI) n20/D of 1.46022. UV absorption at λmax. 480,0 nm.

COMPOSITION EXAMPLES for the inventive, spontaneously dispersible CONCENTRATES containing as antitumoral agents xanthophyll esters according to the formulae (I) to (VI) and rendering, if diluted with water or 5%-glucose solution, thermodynamically stable ULTRAMICROEMULSIONS with MICELLES having a hydrodynamic radius of 1,5 to 3,0 nm.

a) 0,5 to 30% by weight of one or several of the antitumoral agents according to the formulae (I) to (VI)

0,1 to 40% by weight of isopropylmyristate, isopropylpalmitate or Miglyol® 812 (Dynamit Nobel)

0 to 45% by weight of a phosphoric acid ester emulsifier such as Diphasol® 3873 (CIBA-GEIGY) or the identical SERMUL AE 188 (SERVO),

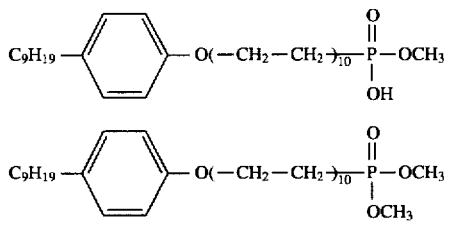

Tenside 508 (CIBA-GEIGY), Zerostat® AN or AT (CIBA-GEIGY), Tinovetin® JU (CIBA-GEIGY), Soprophor® FL (Rhône-Poulenc) 5 to 90% by weight of Invadin® JFC 800% (CIBA-GEIGY)

Miglyol® 812 is a neutral oil (oleum neutrale) of Dynamit Nobel, which is a triacylglycerol of the coconut fatty acids, the so-called fractionated, middle chained ($C_8$ to $C_{10}$) compounds [i.e. a caprylic/capric triglyceride in the CTFA classification].

b) 0,5 to 25% by weight of one or several of the antitumoral agents according to the formulae (I) to (VI)

0,001 to 50% by weight of one or several of the esters corresponding to the general formula

$R^2-COO-R^3$ in which $R^2$ stands for citronellyl, geranyl, farnesyl, phytyl or isophytyl and $R^3$ means a $C_1$ to $C_{32}$ alkyl and a $C_2$ to $C_{32}$ alkenyl group respectively.

0,001 to 90% by weight of a pharmaceutically acceptable tenside or tenside mixture 0 to 10% by weight of a vitamin or provitamin up to 10% of a penetration enhancer or a stabilizer and/or customary auxiliaries and/or diluents.

c) 10% by weight of an oily, antitumoral agent according to the compounds of formulae (I) to (VI)

0 to 20% by weight of isopropylmyristate, isopropylpalmitate or Miglyol® 812 or of one or several of the biotenside esters corresponding to the general formula (XIV)

$R^2-COO-R^3$ in which $R^2$ stands for citronellyl, geranyl, farnesyl, phytyl or isophytyl and $R^3$ means a $C_1$ to $C_{32}$ alkyl and a $C_2$ to $C_{32}$ alkenyl group respectively. 35 to 45% by weight of Invadin® JFC 800%

35 to 45% by weight of Soprophor® FL d) 2 to 5% by weight of a crystalline, antitumoral agent according to the compounds of formulae (I) to (VI)

10 to 20% by weight of isopropylmyristate, isopropylpalmitate or Miglyol® 812 or of one or several of the biotenside esters, corresponding to the general formula (XIV)

$R^2-COO-R^3$ in which $R^2$ stands for citronellyl, geranyl, farnesyl, phytyl or isophytyl and $R^3$ means a $C_1$ to $C_{32}$ alkyl and a $C_2$ to $C_{32}$ alkenyl group respectively.

35 to 45% by weight of Invadin® JFC 800%

35 to 45% by weight of Soprophor® FL and/or Amphonyl CAA and/or a multifunctional glucose derivative, such as Glucate® SS and Glucamate® SSE-20 (AMERCHOL).

Example for the pharmaceutical production of a system's preparation containing the inventive concentrates in the form of "multiple units".

a) Granulation (granules and pellets)

| | |
|---|---|
| Metolose ® 90 SH-4000 (Shin-Etsu Chemical) | 90.0 g |
| Avicel ® PH-101 | 80,3 g |
| Inventive MARIGENOL ® -CONCENTRATE | 139,4 g |
| Aerosil ® 200 | 80,3 g |
| Σ | 390.0 g |

Granulation in the high speed mixer or the fluiidized bed, with the addition of 110 g ethanol, sieving on a 18 to 42 mesh screen with crushing, drying for 24 h at 40° C.

b) Enteric and sustained release coating In the fluidized bed with AQOAT® AS-HG (Shin-Etsu Chemical) and Talc c) Composition of finished granules or micropellets

| Core Material | 44 % by weight |
|---|---|
| Inventive MARIGENOL ® - CONCENTRATE | 25 % by weight |
| Enteric coating | 31 % by weight |
| Σ | 100 % by weight |

N.B. The pellets or granules according to a) can also be filled without prior coating into capsules which are made of AQOAT® (HPMC-AS-M or HPMC-AS-N), have been sealed with acetone/ethanol 1:1 and can thus perform the functions of pH-control and slow release.

P.S.: MARIGENOL® is a trade-mark (™) of MARIGEN S. A., RIEHEN.

BIOLOGICAL ASSAYS.

The antitumour activity of spontaneously dispersible concentrates containing active substances prepared according to the processing examples No. a) to d) and according to the composition examples No. a) to d) is confirmed by the following test results:

1. In-vitro assays using suitable tumour cell lines

A biological assay system using microtiter plates and serial dilutions has been developed. Batches of $10^4$ tumour cells per ml were set up in culture medium RPMI 1640 and inactivated with 10% of fetal calf serum (GIBCO); they are spread at a density low enough to enable them to grow during the assay, in so-called non-confluent monolayers. Samples are added after 6–24 hours, with 100 µl per row, to which 100 µl of medium are added in the first well. Half of this mixture is withdrawn, transferred into the next well and again treated with 100 µl of medium, etc. This results in an n½ geometrical serial dilution.

In the plaque assay, the samples are incubated at 37° C. for 3 to 5 days under 3½% of $CO_2$. They are then stained and fixed using 0.1% crystal violet (Fluka, Buchs) in a solution of 70% of methanol, 1% of formaldehyde and 29% of water. The samples are evaluated under the microscope, magnification 300×. The greatest cytotoxic dilution is determined. The samples can also be evaluated quantitatively by means of scanning and absorption measurement in a spectrophotometer.

| CYTOTOXICITY ASSAY with Py6 cells (virus transformed 3T3-mouse fibroblasts) Testing a 2%-concentrate of varying composition containing PHYSALIEN active substance (ZEAXANTHIN-DI-PALMITATE nat.) | | | |
|---|---|---|---|
| CONCEN-TRATE | after 24 h cell toxic up to: | after 48 h cell toxic up to: | after 72 h cell toxic up to: |
| No. 1 with IPM | 1:800'000 | 1:3'200'000 | 1:6'400'000 |
| No. 2 with C 11-1-CITRON-ELLYL-ESTER | 1:800'000 | 1:6'400'000 | 1:6'400'000 |
| No. 3 with IPM and AOT | 1:800'000 | 1:3'200'000 | 1:6'400'000 |
| No. 4 with C 11:1-CITRO and CAA | 1:1'600'000 | 1:12'800'000 | 1:25'600'000 |

No. 1 2% by weight of PHYSALIEN active substance 12% by weight of IPM 86% by weight of Invadin JFC 800%/Soprophor FL, 50:50
No. 2 with 12% by weight of C 11:1-citronellyl ester instead of IPM, otherwise same composition as No. 1
No. 3 with 86% by weight of Invadin JFC 800%/Soprophor FL/AOT:40:40:20
No. 4 with 12% by weight of C 11:1-citronellyl ester instead of IPM and with 86% by weight of Invadin JFC 800%/Soprophor FL/Amphonyl CAA:40:40:20

Microemulsions 1:10'000 (100 ppm a.s.), i.e. 6 mg a.s. in 60 ml dist. water

N.B.: AOT (Fluka 86139)=Sulfosuccinic acid-bis-2-ethyl-hexylester Na-salt

| CYTOTOXICITY ASSAY with Py6 cells (virus transformed 3T3-mouse fibroblasts) Testing various concentrates of the same composition but containing different Xanthophyll Esters (calculated on a 2%-ester content of the concentrates) | | | |
|---|---|---|---|
| PREPARATION | 48 h Effective in dilution up to 1: | 72 h Effective in dilution up to 1: | 96 h Effective in dilution up to 1: |
| ZEAXANTHIN-DI-UNDECENOATE | 160'000 | 320'000 | 320'000 |
| ISOZEAXANTHIN-DI-UNDECENOATE | 160'000 | 160'000 | 320'000 |
| VIOLAXANTHIN-DI-UNDECENOATE | 160'000 | 160'000 | 320'000 |
| C 11:1-CRYPTOXANTHIN | 320'000 | 320'000 | 640'000 |

VITALITY ASSAY
with human tumor cell lines
A
HL 60: promyelotic LEUKEMIA   1 × 10⁴ cells per well
Proliferation test (Tritium: 1 μCi/pro well H⁺)

| PREPARATION | $10^{-5}$ 0,2 ppm a.s. | $10^{-4}$ 2 ppm a.s. | $10^{-3}$ 20 ppm a.s. |
|---|---|---|---|
| ZEAXANTHIN-DI-UNDECENOATE | 86,0% | 17,4% | 4,0% |
| ISOZEAXANTHIN-DI-UNDECENOATE | 41,2% | 21,2% | 2,6% |
| VIOLAXANTHIN-DI-UNDECENOATE | 44,2% | 26,1% | 3,7% |
| C 11:1-CRYPTOXANTHIN | 32,4% | 12,7% | 2,7% |

RESULTS: %-vitality after 48 hours of exposure to the 2-% MARIGENOL®-CONCENTRATES, taken as aqueous ultramicroemulsions and added once to the medium. When judging the result, one should note that with only 48 h the exposure time was relatively short. Controls 155'421 cpm.

Tests conducted by Dottoressa Anna Guarini, Universit à degli Studi di Torino, Clinica medica.

VITALITY ASSAY
with human tumor cell lines
B
K 562: CHRONIC MYELOID LEUKEMIA
2 × 10⁴ cells per well
Proliferation test (Tritium: 1 μCi/pro well H⁺)

| PREPARATION | $10^{-5}$ 0,2 ppm a.s. | $10^{-4}$ 2 ppm a.s. | $10^{-3}$ 20 ppm a.s. |
|---|---|---|---|
| ZEAXANTHIN-DI-UNDECENOATE | 54,4% | 32,1% | 0% |
| ISOZEAXANTHIN-DI-UNDECENOATE | 82,1% | 11,7% | 0% |
| VIOLAXANTHIN-DI-UNDECENOATE | 28,5% | 10,8% | 0% |
| C 11:1-CRYPTOXANTHIN | 68,6% | 8,2% | 0% |

RESULTS: %-vitality after 48 hours of exposure to the 2-% MARIGENOL®-CONCENTRATES, taken as aqueous ultramicroemulsions and added once to the medium. When judging the result, one should note that with only 48 h the exposure time was relatively short. Controls 501'937 cpm.

Tests conducted by Dottoressa Anna Guarini, Universit à degli Studi di Torino, Clinica medica.

VITALITY ASSAY
with human tumor cell lines
C
TOM MELANOMA   1 × 10⁴ cells pero well
Proliferation test (Tritium: 1 μCi/pro well H⁺)

| PREPARATION | $10^{-5}$ 0,2 ppm a.s. | $10^{-4}$ 2 ppm a.s. | $10^{-3}$ 20 ppm a.s. |
|---|---|---|---|
| ZEAXANTHIN-DI-UNDECENOATE | 74,1% | 65,2% | 21,0% |
| ISOZEAXANTHIN-DI-UNDECENOATE | 63,3% | 65,7% | 12,0% |
| VIOLAXANTHIN-DI-UNDECENOATE | 69,1% | 65,5% | 17,2% |
| C 11:1-CRYPTOXANTHIN | 57,9% | 56,8% | 9,2% |

RESULTS: %-vitality after 48 hours of exposure to the 2-% MARIGENOL®-CONCENTRATES, taken as aqueous ultramicroemulsions and added once to the medium. When judging the result, one should note that with 48 h the time of exposure was relatively short. Controls: 2'262 cpm.

Tests conducted by Dottoressa Anna Guarini, Universit à degli Studi di Torino, Clinica medica.

VITALITÄTY TEST
with human tumor cell-lines
D
Proliferation test (Tritium: 1 μCi/pro well H⁺)
2 × 10⁴ cells per well

| | CELL-LINE | | | | | |
|---|---|---|---|---|---|---|
| | K 562 Concentrate 2% | | HL 60 Concentrate 2% | | ADK Concentrate 2% | |
| PREPARATIONS | $10^{-4}$ | $10^{-5}$ | $10^{-4}$ | $10^{-5}$ | $10^{-4}$ | $10^{-5}$ |
| C 11:1-CRYPTOXAN-THIN | 1.0 | 5.8 | 4.1 | 7.7 | 6.1 | 14.8 |
| C 11:1-ZEAXANTHIN-C 11:1 | 1.5 | 14.9 | 3.3 | 10.4 | 4.5 | 24.7 |
| C 11:1-ISOZEAXAN-THIN-C 11:1 | 0.6 | 1.2 | 4.4 | 5.7 | 1.3 | 4.1 |
| C 12:0-ZEAXANTHIN-C 12:0 | 24.8 | 37.3 | 24.1 | 22.9 | 36.0 | 45.2 |
| C 16:0-ZEAXANTHIN-C 16:0 | 0.7 | 1.0 | 4.3 | 7.5 | 5.9 | 8.4 |
| CONTROLS | 247'125 cpm | | 76'589 cpm | | 57'816 cpm | |

K 562: Leukemia
HL 60: Chronic myeloid Leukemia
ADK: Human Lung Adenocarcinoma

RESULTS: %-vitality after 48 hours of exposure to the 2-% MARIGENOL®-CONCENTRATES, taken as aqueous ultramicroemulsions in dilutions 1:10'000 and 1:100'000 (containing 2,0 ppm and 0,2 ppm active substance, respectively) and added once to the medium. When judging the result, one should note the relatively short exposure time of 48 h.

Tests conducted by Dottoressa Anna Guarini, Universit à degli Studi di Torino, Clinica medica, Torino. 14th to 17th Feb. 1994.

Analytical Proof

1) Identification of the XANTHOPHYLL ESTERS By capillary zone electrophoresis with an instrument of Beckman Instruments, and of BIORAD respectively.
Conditions:

DL-α-Tocopherol 50 mM; buffer pH=9,5 Na-tetra-borate
Run 15 kV, measurement at 195 nm
The ester peak appears after ca. 4 minutes.
Detection limit 0,5 ppm.

2) Identification of the concentrate micelles in the aqueous microemulsion and in the cell plasma of tumour cells after exposure, respectively. Same method as above under 1). The typical peak of the xanthophyll ester compounds contained in the micelles appears after ca. 8 minutes; the delay against the measurement of pure xanthophyll esters is a consequence of the coating of the inner phase of the concentrates and hence of the micelles generated with surfactants. This fact constitutes an important indication of the diffusion behaviour of the inventive ultramicroemulsions.

3) Demonstration of membrane penetration at the tumour cell. With light microscopy (as well as when using electron microscopy) it can be shown that a few hours after incubation (example: Py6 virus transformed 3T3 -mouse fibroblasts; thinly disseminated; medium dilution of the xanthophyll ester concentrates) a corona of vacuoles is forming around the nucleus of the tumour cells.

The analytical demonstration that these vacuoles in fact contain the XANTHOPHYLL ESTER active substances is quite clear and unequivocal: it involves cleaning the incubated tumour cells, extracting the cell plasma with 1% SDS, centrifuging, mixing the supernatant with a 0,05%-solution of Uvitex® CF conc. (CIBA-GEIGY) in acetone/water (85:15) or of Uvitex® EBF (CIBA-GEIGY) or of Tinopal® GS (CIBA-GEIGY).

The XANTHOPHYLL ESTERS according to the invention extinguish the fluorescence in the longwave UV-segment which is normally occasioned by the markers Uvitex® CF conc. and Uvitex® EBF, and Tinopal® GS respectively. The thin-layer plate shows blue coloring.

$^1$H-NMR (300 MHz, CDCl$_3$); 1,04 [CH$_3$ (16,16')]; 1,08 [CH$_3$ (17,17')]; 1,71 [CH$_3$ (18,18')]; 1,98 [CH$_3$ (19,19',20, 20')]; 5,26 [t, two H-C(4,4')]; ca. 5,8–6,2 ppm (Vinylprotones); 0,89 (t, two ω-CH$_3$); 1,27 [s two (CH$_2$)$_9$]; 2,33 (t, two a-CH$_2$].

4.: C$_{72}$H$_{116}$O$_4$ (Mr. 1045,65); mp. 67° C.; VIS (Benzene, qualitative): sh 437, 461,488 nm; UV/VIS (CH$_2$Cl$_2$, quantitative): 280 (22'400), 347 (12'600), sh. 436 (87'900), 459 (119'700), 486 (103'800); IR (CHCl$_3$): 1713 cm$^{-1}$; $^1$H-NMR (300 MHz, CDCl$_3$); 1,03 [CH$_3$ (16,16')]; 1,08 [CH$_3$ (17,17')]; 1,71 [CH$_3$ (18,18')]; 2,34 [CH$_3$ (19,19',20, 20')]; 5,26 [t, two H-C(4,4')]; ca. 6,0–6,7 ppm (Vinylprotones); 0,89 (t, two ω-CH$_3$); 1,27 [s two (CH$_2$)$_{14}$]; 2,34 (t, two a-CH$_2$].

See also R. Entschel und P. Karrer, Helv.Chim.Acta 1958, 41,402.

ANALYTICAL DATA FOR THE PRODUCED ISOZEAXANTHIN ESTERS
Scheme

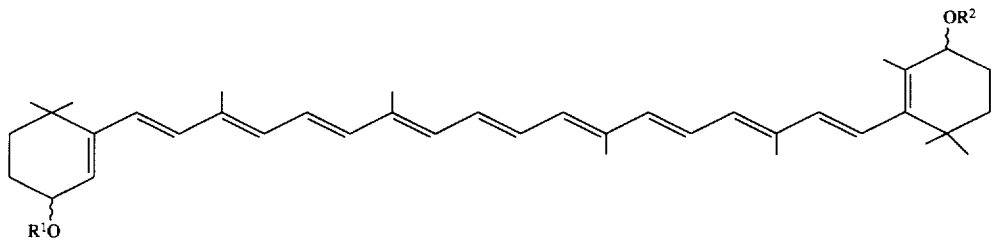

| | | |
|---|---|---|
| 1.: R$^1$ = R$^2$ = CO—CH$_2$—(CH$_2$)$_3$—CH$_3$ (α, ω) | | ISOZEAXANTHIN-bis-CAPRONATE (C 6:0) |
| 2.: R$^1$ = R$^2$ = CO—CH$_2$—(CH$_2$)$_7$—CH=CH$_2$ (α, ψ, ω) | | ISOZEAXANTHIN-bis-10-UNDECENOATE (C 11:1) |
| 3.: R$^1$ = R$^2$ = CO—CH$_2$—(CH$_2$)$_9$—CH$_3$ (α, ω) | | ISOZEAXANTHIN-bis-LAURATE (C 12:0) |
| 4.: R$^1$ = R$^2$ = CO—CH$_2$—(CH$_2$)$_{13}$—CH$_3$ (α, ω) | | ISOZEAXANTHIN-bis-PALMITATE (C 16:0) |

1.: C$_{52}$H$_{76}$O$_4$ (Mr. 765,13); mp. 96° C.; VIS (Benzene, qualitative): sh 426, 460, 487 nm; UV/VIS (CH$_2$Cl$_2$, quantitative): 280 (24'100), 346 (15'750), sh (85'300), 459 (115'500), 486 (100'000); IR (CHCl$_3$): 1720 cm$^{-1}$; $^1$H-NMR (300 MHz, CDCl$_3$); Selection of bands, Numbering of the Carotinoides according to the IUPAC-nomenclature; cf. also the NMR-analysis on (4R,4'R)-Isozeaxanthin by A. Haag and C. H. Eugster, Helv.Chim.Acta 1982, 65, 1795; NMR-Analysis of the Ester components vide Scheme: 1,04 [CH$_3$ (16,16')]; 1,08 [CH$_3$ (17,17')]; 1,76 [CH$_3$ (18, 18')]; 1,98 [CH$_3$ ( 19,19',20,20')]; 5,26 [t,H-C(4,4')]; 6,1–6,7 ppm (Vinyl-protones); 0,91 (t, two ω-CH$_3$); 1,33 [m, two (CH$_2$)$_3$]; 2,33 (t, two a-CH$_2$).

2.: C$_{62}$H$_{92}$O$_4$ (Mr. 901,36); mp. 80° C.; VIS (Benzene, qualitative): sh 437, 460, 488 nm; UV/VIS (CH$_2$Cl$_2$, quantitative): 288 (24'400), 347 (15'500), sh 437 (92'000), 459 (124'600), 487 (107'500); IR (CHCl$_3$): 1718 cm$^{-1}$; $^1$H-NMR (300 MHz, CDCl$_3$); 1,03 [CH$_3$ (16,16')]; 1,08 [CH$_3$ (17,17')]; 1,71 [CH$_3$ (18,18')]; 1,98 [CH$_3$ (19,19',20 20')]; 5,26 [t, H-C(4,4')]; ca. 6,3–6,7 ppm (Vinylprotones); no ω-CH$_3$); 1,31 [s, two (CH$_2$)$_7$]; 2,34 (t, two a-CH$_2$); ca. 4,96 [m, two ω-CH$_2$]; ca. 5,81 [m, two ψ-CH]. 3.: C$_{64}$H$_{100}$O$_4$ (Mr. 933,44); mp. 73° C.; VIS (Benzene, qualitative): sh 440, 461,5, 489 nm; UV/VIS (CH$_2$Cl$_2$, quantitative): 28.0 (23'950), 346 (13'200), sh 436 (93'750), 459 (129'400), 487 (112'500); IR (CHCl$_3$): 1717 cm$^{-1}$;

We claim:

1. A spontaneously dispersible concentrate, which if diluted with water forms a thermodynamically stable ultramicroemulsion with micelles having a hydrodynamic radius of 1.5 to 3 nm, comprising the following components:

0.001 to 30% by weight of a xanthophyll ester selected from the group consisting of formulae (I) to (VI), and combinations thereof:

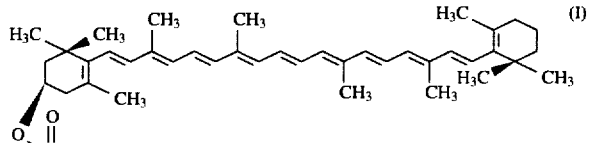

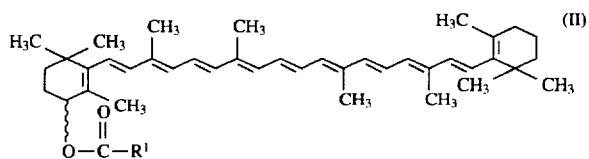

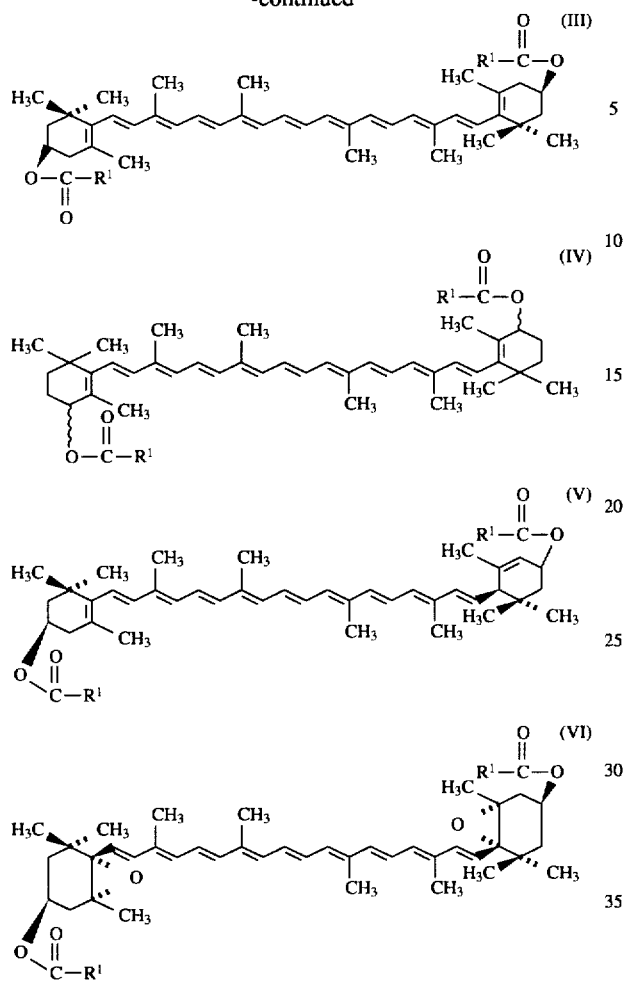

wherein $R^1$ is a $C_1$ to $C_{32}$ alkyl, a $C_2$ to $C_{32}$ alkenyl, a $C_2$ to $C_{32}$ alkapolyene group, or a $C_2$ to $C_{32}$ alkynyl group, 0 to 40% by weight of a solvent or solvent mixture which is pharmaceutically acceptable and acts as a hydrotropic agent or coemulsifier, 0.001 to 90% by weight of a pharmaceutically acceptable surfactant of surfactant mixture, and optionally:

up to 10% by weight of a vitamin or provitamin and up to 10% by weight of a penetration enhancer, stabilizer, excipient and/or a diluent.

2. A spontaneously dispersible concentrate in accordance with claim 1, comprising the following components:

0.5 to 30% by weight of one or several compounds having antitumoral activity and corresponding to formulae (I) to (VI), 1 to 40% by weight of isopropylmyristate, isopropylpalmitate or a neutral oil, 0 to 45% by weight of a phosphoric acid ester tenside, and 5 to 90% by weight of a waterfree tert. octylphenyl polyoxyethylene ether having 9 to 10 oxyethylene groups.

3. A spontaneously dispersible concentrate in accordance with claim 1, comprising the following components:

0.5 to 30% by weight of one or several compounds having antitumoral activity and corresponding to formulae (I) to (VI), 0.001 to 40% by weight of one or several biotenside esters corresponding to the general formula (XIV):

$$R^2—COO—R^3 \qquad (XIV)$$

in which $R^2$ stands for citronellyl, geranyl, farnesyl, phytyl or isophytyl and $R^3$ means a $C_1$ to $C_{32}$ alkyl or a $C_2$ to $C_{32}$ alkenyl group, 0.001 to 90% by weight of a pharmaceutically acceptable tenside or tenside mixture, 0 to 10% by weight of a vitamin or provitamin, and up to 10% by weight of a penetration enhancer, stabilizer, excipient and/or diluent.

4. A spontaneously dispersible concentrate according to claim 1, comprising the following components:

10% by weight of an oily antitumor compound according to the formulae (I) to (VI), 0 to 20% by weight of isopropylmyristate, isopropylpalmitate, a neutral oil or one or a combination of biotenside esters corresponding to the general formula (XIV):

$$R^2—COO—R^3 \qquad (XIV)$$

in which $R^2$ stands for citronellyl, geranyl, farnesyl, phytyl or isophytyl and $R^3$ means a $C_1$ to $C_{32}$ alkyl or a $C_2$ to $C_{32}$ alkenyl group, 35 to 45% by weight of a waterfree tert. octylphenyl polyoxyethelene ether having 9 to 10 oxyethylene groups and 35 to 45% by weight of a surfactant mixture comprising 50% each of the following compounds:

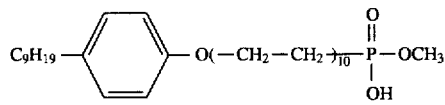

and

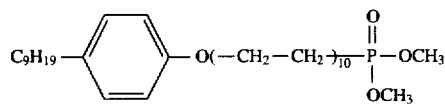

or the tristyryl phenolpolyoxyethylene-18-mono/dimethyl phosphoric acid ester of formula:

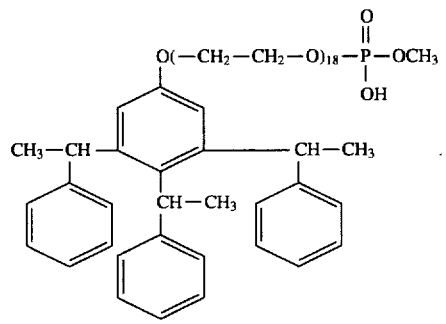

5. A spontaneously dispersible concentrate according to claim 1, comprising the following components:

2 to 5% by weight of a crystalline compound having antitumor activity according to the formulae (I) to (VI), 10 to 20% by weight of isopropylmyristate, isopropylpalmitate, neutral oil or one or a combination of biotenside esters corresponding to the general formula (XIV):

$$R^2—COO—R^3 \qquad (XIV)$$

in which $R^2$ stands for citronellyl, geranyl, farnesyl, phytyl or isophytyl and $R^3$ means a $C_1$ to $C_{32}$ alkyl or a $C_2$ to $C_{32}$ alkenyl group, 35 to 45% by weight of a waterfree tert octylphenyl polyoxyethelene ether having 9 to 10 oxyethylene groups and 35 to 45% by weight of (i) a surfactant mixture of nonylphenol-10-polyoxyethylene-mono/dimethyl phosphoric acid ester or (ii) a tristyryl phenolpolyoxyethylene-18-mono/dimethyl phosphoric acid surfactant.

\* \* \* \* \*